(12) United States Patent
Wang

(10) Patent No.: US 8,753,470 B2
(45) Date of Patent: Jun. 17, 2014

(54) ANALYTE SENSORS AND METHODS OF USE

(75) Inventor: Yi Wang, San Ramon, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 0 days.

(21) Appl. No.: 13/482,675

(22) Filed: May 29, 2012

(65) Prior Publication Data
US 2012/0234487 A1 Sep. 20, 2012

Related U.S. Application Data

(63) Continuation of application No. 13/230,579, filed on Sep. 12, 2011, which is a continuation of application No. 12/463,194, filed on May 8, 2009, now Pat. No. 8,033,162, which is a continuation of application No. 11/615,391, filed on Dec. 22, 2006, now Pat. No. 7,802,467.

(51) Int. Cl.
B32B 38/10 (2006.01)

(52) U.S. Cl.
USPC .......................................... 156/268; 73/61.41

(58) Field of Classification Search
USPC ........ 156/250, 268, 269; 204/403.01, 403.04, 204/403.1, 403.14; 422/82.01, 412; 73/61.41
See application file for complete search history.

(56) References Cited

U.S. PATENT DOCUMENTS

| D331,807 S | 12/1992 | Sodergren |
| D381,591 S | 7/1997 | Rice et al. |
| 6,071,391 A | 6/2000 | Gotoh et al. |
| 6,156,173 A | 12/2000 | Gotoh et al. |
| 6,174,420 B1 | 1/2001 | Hodges et al. |
| 6,270,637 B1 | 8/2001 | Crismore et al. |
| 6,325,975 B1 * | 12/2001 | Naka et al. ..................... 422/430 |
| 6,428,664 B1 | 8/2002 | Bhullar et al. |
| 6,447,657 B1 | 9/2002 | Bhullar et al. |
| 6,503,381 B1 | 1/2003 | Gotoh et al. |
| 6,521,110 B1 | 2/2003 | Hodges et al. |
| 6,541,216 B1 | 4/2003 | Wilsey et al. |
| 6,767,440 B1 | 7/2004 | Bhullar et al. |
| 6,818,180 B2 | 11/2004 | Douglas et al. |
| 6,837,976 B2 | 1/2005 | Cai et al. |
| 6,866,758 B2 | 3/2005 | Bhullar et al. |
| 6,893,545 B2 | 5/2005 | Gotoh et al. |
| 6,923,894 B2 | 8/2005 | Huang et al. |
| 7,008,799 B1 | 3/2006 | Zimmer et al. |
| 7,081,188 B1 | 7/2006 | Cho |
| 7,122,110 B2 | 10/2006 | Deng et al. |
| 7,125,481 B2 | 10/2006 | Musho et al. |
| 7,160,251 B2 | 1/2007 | Neel et al. |
| 7,250,095 B2 | 7/2007 | Black et al. |
| 7,258,769 B2 | 8/2007 | Cui et al. |

(Continued)

FOREIGN PATENT DOCUMENTS

| DE | 20314395 | 11/2003 |
| EP | 1437589 | 7/2004 |

(Continued)

Primary Examiner — Daniel S Larkin
(74) Attorney, Agent, or Firm — Edward J. Baba; Shweta Chandra; Bozicevic, Field & Francis LLP

(57) ABSTRACT

Analyte sensors for determining the concentration of an analyte in a sample. The sensors have a sample chamber having an inlet with a projection extending from an edge of the sensor for facilitating flow of sample into the sample chamber.

27 Claims, 3 Drawing Sheets

(56) References Cited

U.S. PATENT DOCUMENTS

| | | |
|---|---|---|
| 7,299,081 B2 | 11/2007 | Mace et al. |
| 7,527,716 B2 | 5/2009 | Harding |
| 7,892,849 B2 * | 2/2011 | Burke et al. .................. 436/170 |
| 8,061,004 B2 | 11/2011 | Keil |
| 2003/0086073 A1 | 5/2003 | Braig et al. |
| 2004/0186394 A1 | 9/2004 | Roe et al. |
| 2005/0019211 A1 | 1/2005 | Lien |
| 2005/0019212 A1 * | 1/2005 | Bhullar et al. .................. 422/56 |
| 2005/0258052 A1 | 11/2005 | Gotoh et al. |
| 2006/0228263 A1 | 10/2006 | Berndtsson et al. |
| 2007/0108048 A1 | 5/2007 | Wang et al. |
| 2009/0078030 A1 | 3/2009 | Jung |

FOREIGN PATENT DOCUMENTS

| | | | |
|---|---|---|---|
| GB | 2090659 | * | 7/1982 |
| JP | 57132900 | | 8/1982 |
| JP | 11056821 | | 3/1999 |
| WO | 0173395 | | 10/2001 |
| WO | 2005043133 | | 5/2005 |

* cited by examiner

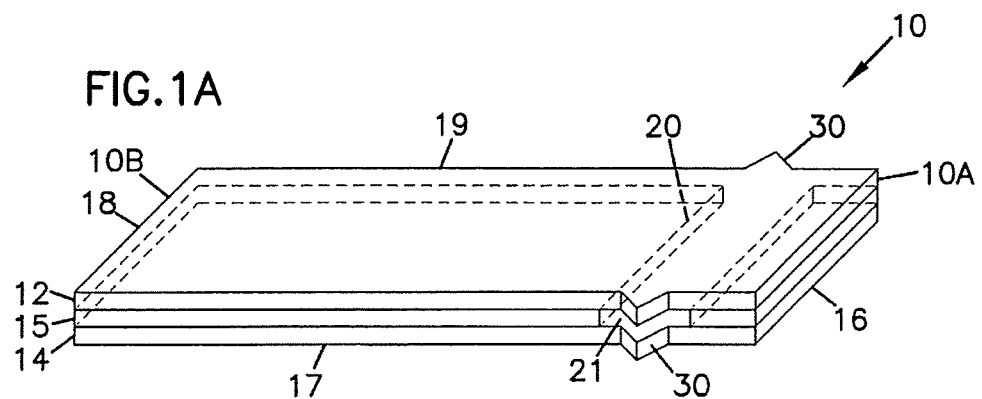
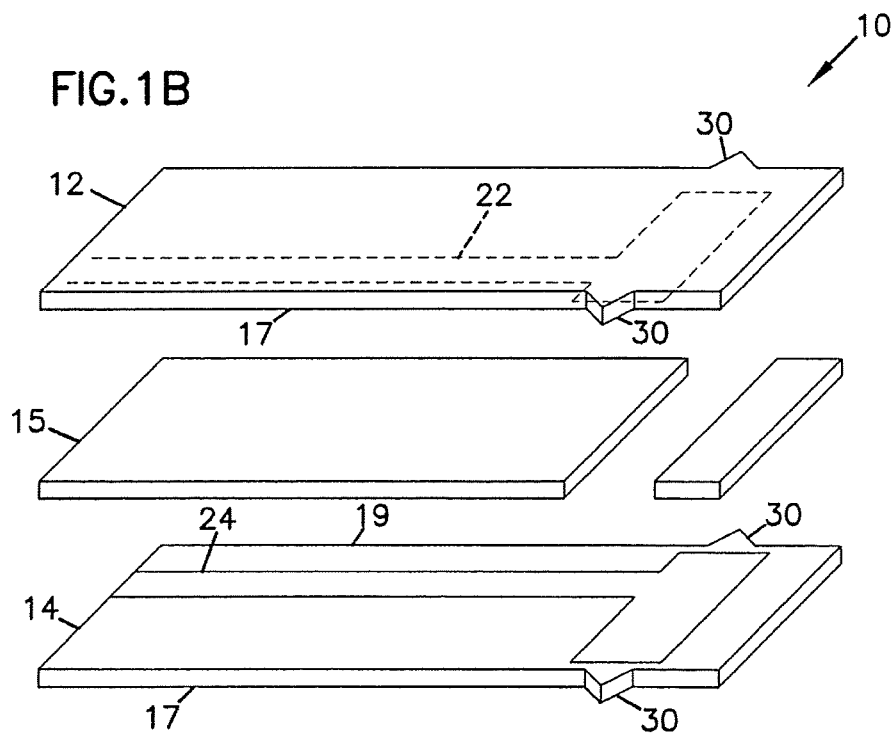

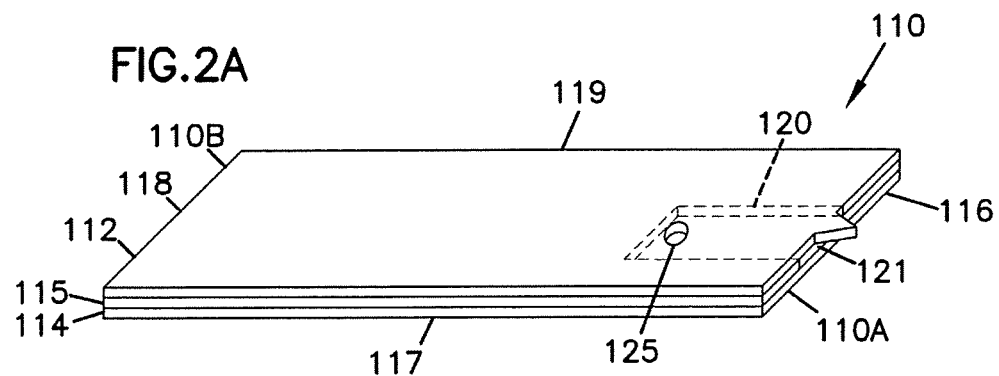
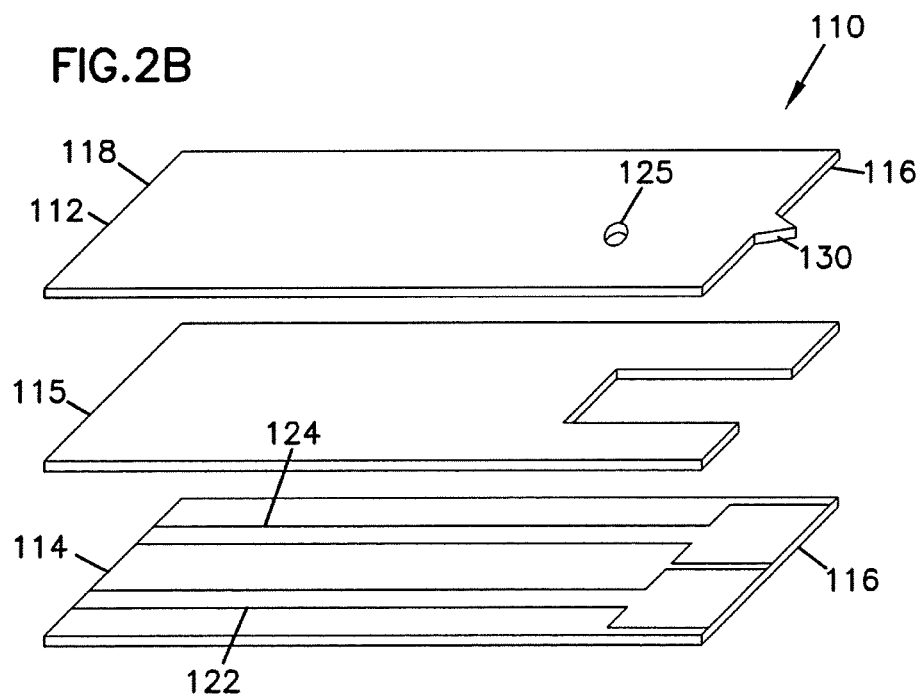

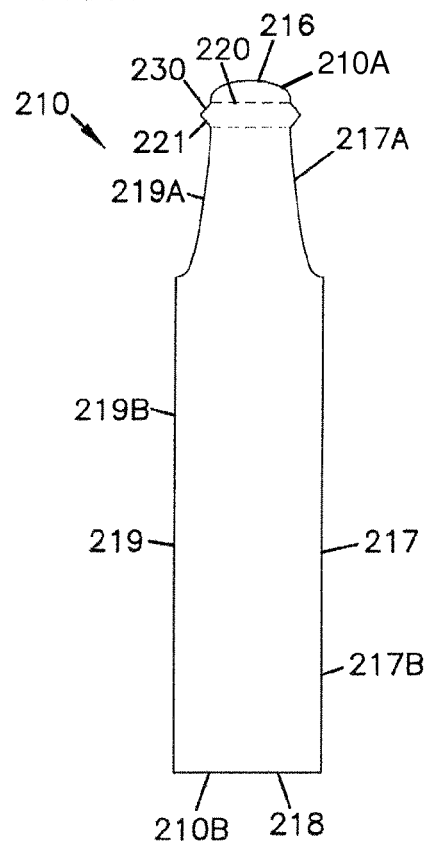
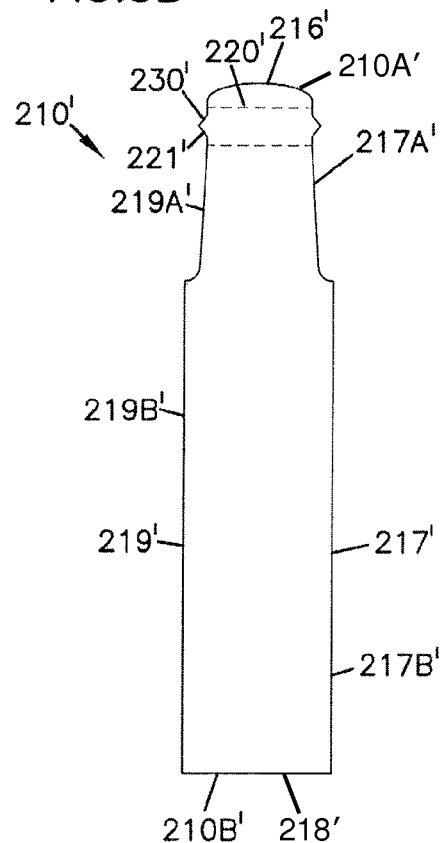
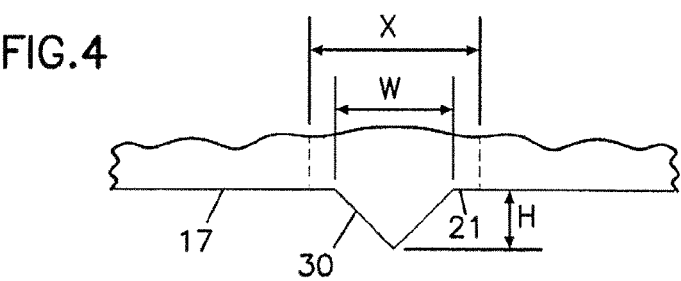

ANALYTE SENSORS AND METHODS OF USE

CROSS-REFERENCE TO RELATED APPLICATIONS

This application is a continuation of U.S. patent application Ser. No. 13/230,579 filed on Sep. 12, 2011, which is a continuation of U.S. patent application Ser. No. 12/463,194, filed on May 8, 2009, now U.S. Pat. No. 8,033,162, which is a continuation of U.S. patent application Ser. No. 11/615,391, filed on Dec. 22, 2006, now U.S. Pat. No. 7,802,467, all of which are incorporated herein by reference.

FIELD OF THE INVENTION

This invention relates to analytical sensors for the detection of analyte in a sample, and methods of making and using the sensors.

BACKGROUND

Biosensors, also referred to as analytical sensors or merely sensors, are commonly used to determine the presence and concentration of a biological analyte in a sample. Such biosensors are used, for example, to monitor blood glucose levels in diabetic patients.

As sensors continue to be used, there continues to be an interest in sensors that are easy to manufacture and easy for a patient to use.

SUMMARY

The present disclosure provides sensors and methods for the detection and quantification of an analyte in a sample. The sensors have an inlet to the sample chamber that facilitates drawing of sample (e.g., blood) into the chamber. The sensors include an element that provides an open path to the sample chamber and that inhibits restriction of the inlet by the patient's skin.

In general, certain embodiments of the invention include sensors for analysis of an analyte in a sample, e.g., a small volume sample, by, for example, coulometry, amperometry and/or potentiometry. The sensors include at least a working electrode and a counter electrode, which may be on the same substrate (e.g., co-planar) or may be on different substrates (e.g., facing). Sensing chemistry may be present on the electrode(s). The sensors also include a sample chamber to hold the sample in electrolytic contact with the working electrode. An inlet, present in an edge of the sensor, provides fluid communication to the sample chamber. The sensors may be configured for side-filling or tip-filling. In addition, in some embodiments, the sensor may be part of an integrated sample acquisition and analyte measurement device. An integrated sample acquisition and analyte measurement device may include a sensor and a skin piercing member, so that the device can be used to pierce the skin of a user to cause flow of a fluid sample, such as blood, that may then be collected by the sensor.

In one particular aspect, the disclosure is directed to an analyte sensor for determining the concentration of an analyte in a sample, the sensor comprising a sample chamber having an inlet with a width and an element such as projection extending from an edge of the sensor, the projection having a height and a width. The width of the projection may be the same or more than the inlet width, or may be less than the inlet width, e.g., no more than about 80% of the inlet width, e.g., no more than about 75% or about 50% of the inlet width. The average projection width may be no more than about 50% of the inlet width, or no more than about 40%. The height of the projection may be at least about 0.1 mm or at least about 0.2 mm. The projection may extend from a side edge of the substrate or from an end edge of the substrate. In some embodiments, the sensor includes a second projection.

In another particular aspect, the disclosure is directed to an analyte sensor having a first substrate, a second substrate, and a spacer layer therebetween, with a sample chamber defined between the first substrate and the second substrate bounded by the spacer layer. The sample chamber has at least one inlet, and a protrusion extending from the first substrate at the inlet. The sensor may include second, third and/or fourth protrusions.

In yet another particular aspect, the disclosure is directed to an analyte sensor for determining the concentration of an analyte in a sample, the sensor having a first substrate and a second substrate each having a first side edge and a second side edge, a sample chamber defined between the first substrate and the second substrate, with the sample chamber extending from the first side edge to the second side edge, a first aperture and a second aperture between the first substrate and the second substrate at the first side edge and the second side edge, respectively, and a first projection and a second projection extending from the first side edge of the first substrate and the second side edge of the first substrate, respectively, proximate the apertures, each of the projections having a width less than the width of the proximate aperture. The sensor may additionally have a third projection and a fourth projection extending from the first side edge of the second substrate and the second side edge of the second substrate, respectively, proximate the apertures. The maximum width of the projection may be no more than about 80% of the aperture width, e.g., no more than about 75% or about 50% of the aperture width. The average projection width may be no more than about 50% of the inlet width, or no more than about 40%. The height of the projections may be at least about 0.1 mm or at least about 0.2 mm.

The sensors may have a sample chamber volume of no more than about one microliter, and in some embodiments, a volume of no more than about 0.5 microliter.

Methods of using the sensors include determining the concentration of glucose.

These and various other features which characterize the invention are pointed out with particularity in the attached claims. For a better understanding of the invention, its advantages, and objectives obtained by its use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views:

FIG. 1A is a schematic perspective view of a first embodiment of a sensor strip in accordance with the present invention;

FIG. 1B is an exploded view of the sensor strip of FIG. 1A, the layers illustrated individually with the electrodes in a first configuration;

FIG. 2A is a schematic view of a second embodiment of a sensor strip in accordance with the present invention;

FIG. 2B is an exploded view of the sensor strip of FIG. 2A, the layers illustrated individually with the electrodes in a second configuration;

FIG. 3A is a schematic top view of a third embodiment of a sensor strip in accordance with the present invention;

FIG. 3B is a schematic top view of a fourth embodiment of a sensor strip in accordance with the present invention; and FIG. 4 is an enlarged top plan view of a portion of a sensor strip according to the present invention.

DETAILED DESCRIPTION

This disclosure provides sensors and methods of making and using those sensors that facilitate the drawing of fluid sample (e.g., blood) into the sensor by inhibiting contact of the patient's skin with the sample inlet.

Referring to the drawings in general and FIGS. 1A and 1B in particular, a first embodiment of a sensor 10 is schematically illustrated, herein shown in the shape of a strip. It is to be understood that the sensor may be any suitable shape. Sensor strip 10 has a first substrate 12, a second substrate 14, and a spacer 15 positioned therebetween. Sensor strip 10 is a layered construction.

Sensor strip 10 includes at least one working electrode 22 and at least one counter electrode 24. Although not illustrated, sensor strip 10 may also include an optional fill indicator electrode and/or and optional insertion monitor.

Sensor strip 10 has a first, distal end 10A and an opposite, proximal end 10B. At distal end 10A, sample to be analyzed is applied to sensor 10. Distal end 10A could be referred as 'the fill end', 'sample receiving end', or similar. Proximal end 10B of sensor 10 is configured for operable, and usually releasable, connecting to a device such as a meter. Sensor strip 10, in certain embodiments, has a generally rectangular shape, i.e., its length is longer than its width, although other shapes 10 are possible as well, as noted above. Sensor strip 10 has four edges, end edge 16 at distal end 10A, end edge 18 at proximal end 10, and side edges 17, 19 extending therebetween.

The dimensions of a sensor may vary. In certain embodiments, the overall length of sensor strip 10, from end edge 16 to end edge 18, may be no less than about 10 mm and no greater than about 50 mm. For example, the length may be between about 30 and 45 mm; e.g., about 30 to 40 mm. It is understood, however that shorter and longer sensor strips 10 could be made. In certain embodiments, the overall width of sensor strip 10, from side edge 17 to side edge 19, may be no less than about 3 mm and no greater than about 15 mm. For example, the width may be between about 4 and 10 mm, about 5 to 8 mm, or about 5 to 6 mm. In one particular example, sensor strip 10 has a length of about 32 mm and a width of about 6 mm. In another particular example, sensor strip 10 has a length of about 40 mm and a width of about 5 mm. In yet another particular example, sensor strip 10 has a length of about 34 mm and a width of about 5 mm.

The sensor includes a sample chamber for receiving a volume of sample to be analyzed; in the embodiment illustrated, particularly in FIG. 1A, sensor strip 10 includes sample chamber 20 having an inlet 21 for access to sample chamber 20. In the embodiment illustrated, sensor strip 10 is a side-fill sensor strip, having inlet 21 present on side edge 17 of strip 10. In this embodiment, sensor strip 10 has a second inlet at side edge 19 (not seen). Tip-fill sensors, having an inlet at, for example, end edge 16, are also within the scope of this disclosure, as well as corner fill sensors.

Proximate inlet 21, sensor strip 10 includes an element for facilitating the drawing of fluid sample (e.g., blood) into sensor strip 10 by inhibiting contact of the patient's skin with sample inlet 21. Sensor strip 10 includes a projection 30 extending outward from at least one of substrates 12, 14 in the location of inlet 21. In this embodiment, projection 30 is present on both substrates, substrate 12 and substrate 14, and on both side edges, edge 17 and edge 19. Additional discussion of projection 30 is provided below. In some embodiments, the element (e.g., projection 30) may facilitate the drawing of fluid sample (e.g., blood) into sensor strip 10 by capillary fluid flow mechanism.

Referring to FIGS. 2A and 2B, an alternate embodiment of a sensor is illustrated as sensor strip 110. Similar to sensor strip 10, sensor strip 110 has a first substrate 112, a second substrate 114, and a spacer 115 positioned therebetween. Sensor strip 110 includes at least one working electrode 122 and at least one counter electrode 124, in this embodiment, both on substrate 114.

Sensor strip 110 has a first, distal end 110A and an opposite, proximal end 110B. At distal end 110A, sample to be analyzed is applied to sensor 110. Distal end 110A could be referred as 'the fill end', 'sample receiving end', or similar. Proximal end 110B of sensor 110 is configured for operable, and preferably releasable, connecting to a device such as a meter. Similar to sensor strip 10, sensor strip 110 is a layered construction, in certain embodiments having a generally rectangular shape, which is formed by first and second substrates 112, 114 and defined by end edges 116, 118 and side edges 117, 119. The discussion above about substrates 12, 14 and spacer 15 and the various features applies to substrates 112, 114 and spacer 115 and the various features.

Similar to sample chamber 20 of sensor strip 10, sensor strip 110 includes sample chamber 120 defined by substrate 112, substrate 114 and spacer 115. Sample chamber 120 includes an inlet 121 for access to sample chamber 120. Sensor strip 110 is a tip-fill sensor, having inlet 121 in end edge 116 at end 110A. Extending from sample chamber 120, through substrate 112, is a vent 125. The discussion above about sample chamber 20 and its measurement zone also applies to sample chamber 120.

Proximate inlet 121, sensor strip 110 includes an element for facilitating the drawing of fluid sample (e.g., blood) into sensor strip 110 by inhibiting contact of the patient's skin with sample inlet 121. Sensor strip 110 includes a projection 130 extending outward from at least one of substrates 112, 114 in the location of inlet 121. In this embodiment, projection 130 is present on only one substrate, substrate 112. Additional discussion of projection 130 is provided below.

Referring to FIGS. 3A and 3B, two other alternate embodiments of sensors are illustrated as sensor strips 210, 210', respectively. Similar to sensor strips 10, 110 discussed before, sensor strips 210, 210' have a first substrate, a second substrate, and a spacer positioned therebetween. Sensor strips 210, 210' include at least one working electrode and at least one counter electrode.

Sensor strips 210, 210' have a first, distal end 210A, 210A' and an opposite, proximal end 210B, 210B'. Similar to sensor strips 10, 110, sensor strips 210, 210' are layered constructions, in this embodiment, having a generally rectangular shape with a width at proximal end 210B, 210B' and a reduced width closer to distal end 210A, 210A'. The shape of sensor strip 210, 210' is defined by end edges 216, 216', 218, 218' and side edges 217, 217', 219, 219'. Each of side edges 217, 217', 219, 219' has a first portion where edges 217A, 217A', 219A, 219A' are recessed or reduced (e.g., the sensor width is reduced in the first portion) as compared to a second portion, defined by edges 217B, 217B', 219B, 218B', where the width is the entire width of the sensor.

Edges 217A, 217A', 219A, 219A' in the first portion may have generally any shape, such as linear, arcuate (e.g., concave or convex), or irregular. Sections of the portion may have side edges 217A, 217A', 219A, 219A' angled (e.g., tapered) or parallel to each other. Strip 210, of FIG. 3A, has non-parallel, arcuate edges 217A, 219A in the first portion, whereas strip 210' of FIG. 3B has generally parallel, generally linear edges 217A', 219A', having an arcuate transition region proximate edges 217B', 219B'. Having a recessed or reduced portion, such as defined by edges 217A, 217A', 219A, 219A', facilitates differentiating distal end 210A, 210A' from proximal end 210B, 210B'.

Similar to the previous sensor embodiments, sensor strips 210, 210' include a sample chamber 220, 220' defined by the substrates and the spacer. Sample chambers 220, 220' include an inlet 221, 221' for access thereto. Sensor strips 210, 210' are side-fill sensors, having two inlets 221, 221', one in edge 217A, 217A' and one in edge 219A, 219A' proximate end 210A, 210A'.

Proximate inlet 221, 221', sensor strips 210, 210' include an element for facilitating the drawing of fluid sample (e.g., blood) into sensor strips 210, 210' by inhibiting contact of the patient's skin with sample inlet 221, 221'. Sensor strips 210, 210' include a projection 230, 230' extending outward from at least one of substrates in the location of inlet 221, 221'. In this embodiment, projection 230, 230' is present on only one substrate, substrate, at both inlets 221. Additional discussion of projection 230, 230' is provided below.

The following detailed discussion applies to both sensor strip 10 and sensor strips 110, 210, 210' and their various elements and features. Although the following discussion usually uses the references numerals for sensor strip 10 (e.g., substrates 12, 14, sample chamber 20, inlet 21, etc.), it is to be understood that this discussion applies to both embodiments, i.e., sensor strip 10, sensor strip 110 and sensor strips 210, 210'.

Substrates and Spacer

As provided above, sensor strip 10 has first and second substrates 12, 14, non-conducting, inert substrates which form the overall shape and size of sensor strip 10. The substrates may be substantially rigid or substantially flexible. In certain embodiments, the substrates are flexible or deformable. Examples of suitable materials for the substrates include, but are not limited to, polyester, polyethylene, polycarbonate, polypropylene, nylon, and other "plastics" or polymers. In certain embodiments the substrate material is MELINEX polyester. Other non-conducting materials may also be used.

As indicated above, positioned between substrate 12 and substrate 14 may be spacer 15 to separate first substrate 12 from second substrate 14. In some embodiments, spacer 15 extends from end 10A to end 10B of the sensor strip, or extends short of one or both ends. The spacer is an inert non-conducting substrate, typically at least as flexible and deformable (or as rigid) as the substrates. In certain embodiments, the spacer is an adhesive layer or double-sided adhesive tape or film that is continuous and contiguous. Any adhesive selected for the spacer should be selected to not diffuse or release material which may interfere with accurate analyte measurement.

In certain embodiments, the thickness of the spacer may be constant throughout, and may be at least about 0.01 mm (10 µm) and no greater than about 1 mm or about 0.5 mm. For example, the thickness may be between about 0.02 mm (20 µm) and about 0.2 mm (200 µm). In one certain embodiment, the thickness is about 0.05 mm (50 µm), and about 0.1 mm (100 µm) in another embodiment.

Sample Chamber

The sensor includes a sample chamber for receiving a volume of sample to be analyzed; access to the sample chamber is provided via an inlet. The sample chamber is configured so that when a sample is provided in the chamber, the sample is in electrolytic contact with both a working electrode and a counter electrode, which allows electrical current to flow between the electrodes to effect the electrolysis (electrooxidation or electroreduction) of the analyte.

Sample chamber 20 is defined by substrate 12, substrate 14 and spacer 15; in many embodiments, sample chamber 20 exists between substrate 12 and substrate 14 where spacer 15 is not present. Typically, a portion of the spacer is removed to provide a volume between the substrates without the spacer; this volume of removed spacer is the sample chamber. For embodiments that include a spacer between the substrates, the thickness of the sample chamber is generally the thickness of the spacer.

The sample chamber has a volume sufficient to receive a sample of biological fluid therein. In some embodiments, such as when a sensor is a small volume sensor, the sample chamber has a volume that is typically no more than about for example no more than about 0.5 µL and also for example, no more than about 0.25 µL. A volume of no more than about 0.1 µL is also suitable for the sample chamber, as are volumes of no more than about 0.05 µL and about 0.03 µL.

A measurement zone is contained within the sample chamber and is the region of the sample chamber that contains only that portion of the sample that is interrogated during the analyte assay. In some designs, the measurement zone has a volume that is approximately equal to the volume of the sample chamber. In some embodiments the measurement zone includes 80% of the sample chamber, 90% in other embodiments, and about 100% in yet other embodiments.

As provided above, the thickness of the sample chamber corresponds typically to the thickness of any spacer. Particularly for facing electrode configurations, as in the sensor illustrated in FIG. 1B, this thickness is small to promote rapid electrolysis of the analyte, as more of the sample will be in contact with the electrode surface for a given sample volume. In addition, a thin sample chamber helps to reduce errors from diffusion of analyte into the measurement zone from other portions of the sample chamber during the analyte assay, because diffusion time is long relative to the measurement time, which may be about five seconds or less.

Electrodes

The sensor includes a working electrode and at least one counter electrode. The counter electrode may be a counter/reference electrode. If multiple counter electrodes are present, one of the counter electrodes will be a counter electrode and one or more may be reference electrodes.

For sensor 10, at least one working electrode is positioned on one of first substrate 12 and second substrate 14 in the measurement zone and/or sample chamber. In FIG. 1B, working electrode 22 is illustrated on substrate 12. Working electrode 22 extends from the sample chamber 20, proximate distal end 10A, to the other end of the sensor 10, end 10B, as an electrode extension called a "trace". The trace provides a contact pad for providing electrical connection to a meter or other device to allow for data and measurement collection.

For sensor 110, at least one working electrode is positioned on one of first substrate 112 and second substrate 114 in the measurement zone and/or sample chamber. In FIG. 2B, working electrode 122 is illustrated on substrate 114. Working electrode 122 extends from the sample chamber, proximate distal end 110A, to the other end of the sensor 110, end 110B, as an electrode extension called a "trace". The trace provides a contact pad for providing electrical connection to a meter or other device to allow for data and measurement collection.

Working electrode 22, 122 may be a layer of conductive material such as gold, carbon, platinum, ruthenium dioxide, palladium, or other non-corroding, conducting material. The working electrode may be a combination of two or more conductive materials. An example of a suitable conductive epoxy is ECCOCOAT CT5079-3 Carbon-Filled Conductive Epoxy Coating (available from W.R. Grace Company, Woburn, Mass.). The material of the working electrode typically has relatively low electrical resistance and is typically electrochemically inert over the potential range of the sensor during operation.

The working electrode may be applied on the substrate by any of various methods, including by being deposited, such as by vapor deposition or vacuum deposition or otherwise sputtered, printed on a flat surface or in an embossed or otherwise recessed surface, transferred from a separate carrier or liner, etched, or molded. Suitable methods of printing include screen-printing, piezoelectric printing, ink jet printing, laser printing, photolithography, and painting.

The sensor also includes at least one counter electrode positioned within the measurement zone and/or sample chamber. In FIG. 1B, counter electrode 24 is illustrated on substrate 14. Counter electrode 24 extends from the sample chamber 20, proximate first end 10A, to the other end of the sensor 10, end 10B, as an electrode extension called a "trace". The trace provides a contact pad for providing electrical connection to a meter or other device to allow for data and measurement collection. In FIG. 2B, counter electrode 124 is illustrated on substrate 114. Counter electrode 124 extends from the sample chamber, proximate first end 110A, to the other end of the sensor 110, end 110B, as an electrode extension called a "trace". The trace provides a contact pad for providing electrical connection to a meter or other device to allow for data and measurement collection.

Counter electrodes 24, 124 may be constructed in a manner similar to working electrodes 22, 122. Suitable materials for the counter/reference or reference electrode include Ag/AgCl or Ag/AgBr on a non-conducting base material or silver chloride on a silver metal base. The same materials and methods may be used for the counter electrode as are available for the working electrode, although different materials and methods may also be used. The counter electrode may include a mix of multiple conducting materials, such as Ag/AgCl and carbon.

The working electrode and counter electrode may be positioned opposite to and facing each other to form facing electrodes. See for example, FIG. 1B, which has working electrode 22 on substrate 12 and counter electrode 24 on substrate 14, forming facing electrodes. In this configuration, the sample chamber is typically present between the two electrodes 22, 24. In other embodiments, the working electrode and counter electrode may be positioned generally planar to one another, such as on the same substrate, to form co-planar or planar electrodes. See for example, FIG. 2B, which has both working electrode 122 and counter electrode 124 on substrate 114, forming planar electrodes.

In some instances, it is desirable to be able to determine when the sample chamber of the sensor is sufficiently filled with sample. Sensor strip 10 may be indicated as filled, or substantially filled, by observing a signal between an optional indicator (or fill) electrode and one or both of working electrode 22 or counter electrode 24 as sample chamber 20 fills with fluid. When fluid reaches the indicator electrode, the signal from that electrode will change. Suitable signals for observing include, for example, voltage, current, resistance, impedance, or capacitance between the indicator electrode and, for example, working electrode 22. Alternatively, the sensor may be observed after filling to determine if a value of the signal (e.g., voltage, current, resistance, impedance, or capacitance) has been reached indicating that the sample chamber is filled.

For side-fill sensors, such as sensor 10 of FIGS. 1A and 1B and sensor 210 of FIG. 3, an indicator electrode may be present on each side of the counter electrode. This permits the user to fill the sample chamber from either the left or right side with an indicator electrode disposed further upstream. This three-electrode configuration is not necessary. Side-fill sensors may also have a single indicator electrode and may include some indication as to which side should be placed in contact with the sample fluid.

The indicator electrode may also be used to improve the precision of the analyte measurements. The indicator electrode may operate as a working electrode or as a counter electrode or counter/reference electrode. Measurements from the indicator electrode/working electrode may be combined (e.g., added or averaged) with those from the first counter/reference electrode/working electrode to obtain more accurate measurements.

The sensor or equipment that the sensor connected is with (e.g., a meter) may include a signal (e.g., a visual sign or auditory tone) that is activated in response to activation of the indicator electrode to alert the user that the desired zone has been filled. The sensor or equipment may be configured to initiate a reading when the indicator electrode indicates that the measurement zone has been filled with or without alerting the user. The reading may be initiated, for example, by applying a potential between the working electrode and the counter electrode and beginning to monitor the signals generated at the working electrode.

Sensing Chemistry

In addition to working electrode 22, sensing chemistry material(s) are preferably provided in sample chamber 20 for the analysis of the analyte. Sensing chemistry material facilitates the transfer of electrons between working electrode 22 and the analyte in the sample. Any sensing chemistry may be used in the sensor; the sensing chemistry may include one or more materials.

The sensing chemistry may be diffusible or leachable, or non-diffusible or non-leachable. For purposes of discussion herein, the term "diffusible" will be used to represent "diffusible or leachable" and the term "non-diffusible" will be used to represent "non-diffusible or non-leachable" and variations thereof. Placement of sensing chemistry components may depend on whether they are diffusible or not. For example, both non-diffusible and/or diffusible component(s) may form a sensing layer on the working electrode. Alternatively, one or more diffusible components may be present on any surface in the sample chamber prior to the introduction of the sample to be analyzed. As another example, one or more diffusible component(s) may be placed in the sample prior to introduction of the sample into the sample chamber.

The sensing chemistry generally includes an electron transfer agent that facilitates the transfer of electrons to or from the analyte. The electron transfer agent may be diffusible or non-diffusible, and may be present on working electrode 22 as a layer. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes may be used for other analytes.

The electron transfer agent, whether it is diffusible or not, facilitates a current between the working electrode and the analyte and enables the electrochemical analysis of molecules. The agent facilitates the transfer electrons between the electrode and the analyte.

This sensing chemistry may, additionally to or alternatively to the electron transfer agent, include a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator may be a polymeric redox mediator or a redox polymer (i.e., a polymer having one or more redox species). Examples of suitable redox mediators and redox polymers are disclosed in U.S. Pat. No. 6,338,790, for example, and in U.S. Pat. Nos. 6,605,200 and 6,605,201.

If the redox mediator is non-diffusible, then the redox mediator may be present on the working electrode as a layer. In an embodiment having a redox mediator and an electron transfer agent, if the redox mediator and electron transfer agent are both non-leachable, then both components are on the working electrode as individual layers, or combined and applied as a single layer.

The redox mediator, whether diffusible or not, mediates a current between the working electrode and the analyte and enables the electrochemical analysis of molecules which may not be suited for direct electrochemical reaction on an electrode. The mediator functions as an agent to transfer electrons between the electrode and the analyte.

In accordance with this disclosure, sensors, such as sensor strips 10, 110, 210, 210' include projection 30, 130, 230, 230' for facilitating the drawing of fluid sample (e.g., blood) into the sensor by inhibiting contact of the patient's skin with the sample inlet. Projection 30 is an element extending outward from at least one of substrates 12, 14 in the location of sample chamber inlet 21. Projection 30 extends out from the edge in which the inlet is present. For example, projection 30 extends out from edge 17 and edge 19 of both substrates 12, 14; projection 130 extends out from edge 116 of substrate 112; and projections 230, 230' extend out from edges 217A, 217A', 219A, 219A'.

Referring to FIG. 4, a generic projection is illustrated. This may be projection 30 extending from edge 17 or from edge 19, projection 130 extending from edge 116, projection 230 extending from edge 217A or edge 219A, or projection 230' extending from edge 217A' or edge 219A'. However to facilitate discussion, the projection in FIG. 4 will be referred to as projection 30 ending from edge 17, although it should be understood that the project and edge could be any of those described herein. Similarly, to facilitate discussion, the inlet will be referred to as inlet 21.

Projection 30 extends from edge 17 at inlet 21. Projection 30 may be additionally or alternately referred to as an outward notch, a protrusion, an overhang, a cantilever, a tab, or other similar term that describes an element extending out from the sensor. Projection 30 inhibits blocking or sealing of inlet 21 by the skin of the sensor user. The small, protrusion of projection 30 out from edge 17 inhibits the user's skin from blocking the inlet and maintains a passage between the skin and inlet 21 for fluid sample to flow to the sample chamber. Additionally, projection 30 may function as a visual and/or tactile indicator to the user as to the location of inlet 21.

For layered sensors, such as sensor strips 10, 110, 210, 210' projection 30 can be present on both substrates (e.g., substrates 12, 14) or only one substrate.

The shape and size of projection 30 is selected so that the user's skin cannot readily conform around projection 30, thus blocking access to inlet 21 between the substrates.

Projection 30 has a width W, measured in the same direction as a width X of inlet 21. In this embodiment, inlet 21 has the same width X as its sample chamber. In some embodiments, projection 30 may extend over the entire width X of inlet 21; i.e., width W is the same or more than width X. In other embodiments, however, the maximum width W of projection 30 is less than width X of inlet 21, and in this embodiment, less than the width of the sample chamber. It is understood that in some embodiments, the width of the sample chamber may be greater or smaller than width X of inlet 21. The maximum width W of projection 30, in some embodiments, is no more than 80% of width X of inlet 21, often no more than 75%. In some embodiments, the maximum width W is no more than 70% of width X. In other embodiments, the maximum width W is no more than 60% of width X. In still other embodiments, the maximum width W is no more than 50% of the width X of inlet 21. In other embodiments, the average width W of projection 30 is no more than 50% of width X. For example, the average width W is no more than 45% of width X, and in some embodiments no more than 40% of width X. In some embodiments, maximum width W is no more than about 1.5 mm, e.g., no more than about 1 mm, e.g., no more than about 0.5 mm.

Projection 30 also has a height, the distance from side edge 17 that projection 30 extends. Height H of projection 30 is at least 0.1 mm, often at least 0.2 mm, e.g., at least 0.3 mm. Typically, the larger the height H, the better the passage created due to projection 30.

The ratio of width W to height H, in some embodiments, is about 2:1 to about 1:2. In other embodiments, the ratio of width W to height H is about 1.5:1 to about 1:1.5.

In the illustrated embodiment of FIG. 4, projection 30 has a triangular shape, with its base even with edge 17 and its apex pointing away from inlet 21. In some embodiments, the apex may be defined by a radius. Other configurations for projection 30 are suitable, such as rectangular (including square), arcuate (e.g., semi-circular), pentagon, etc. Geometric shapes could have arcuate sides; for example, a substantially triangular or triangular-like projection could have arcuate (e.g., concave or convex) sides; other shapes could additionally have arcuate side(s). Projection 30 may be symmetrical or unsymmetrical. In some embodiments, however, projection 30 has an apex or point extending away from inlet 21; the apex may have a radius associate with it. Geometric shapes such as triangles, pentagons, etc., have an apex. A configuration such as projection 30 provides a small area (e.g., a point) for contacting the skin of the sensor user.

In some embodiments, the extension or cantilever of projection 30 out from edge 17 facilitates drawing of sample into inlet 21 and the sample chamber. Details regarding using a cantilevered sensor for facilitating sample flow are discussed in U.S. Pat. No. 7,846,311.

In one particular exemplary embodiment, a triangular projection 30 has a height H of about 0.38 mm (15 mil) and a width W of about 0.5 mm (20 mil), whereas inlet 21 has a width X of about 1 mm (40 mil). In this embodiment, projection 30 has a width that is about 50% of the inlet width. The ratio of width W to height H is 4:3, or, about 1.33:1.

Various specific configurations of sensors having projections are illustrated in U.S. Design Pat. No. D587,142, the entire disclosure of which is incorporated herein by reference.

General Method for Manufacturing Sensors

Sensor strips 10, 110, 210, 210' discussed above, are sandwiched or layered constructions having substrates 12, 14, 112, 114 spaced apart, such as by spacer 15, 115. Such a construction may be made by laminating the various layers together, in any suitable manner. Projection 30, 130, etc. may be formed on substrate(s) 12, 14, etc. before lamination, or, the overall shape of sensor strips 10, 110, etc. may be formed (e.g., punched) after lamination of the various layers together. An alternate method for making sensor strips 10, 110, 210, 210' and other sensors in accordance with the invention, is to mold the sensors.

Molding may include positioning at least two spaced apart electrically conductive electrodes (e.g., wires) in a mold, and molding a body of insulative material around the electrodes, with one end having therein means for receiving a fluid sample. More specifically, molding could include positioning at least two spaced apart electrically conductive electrodes (e.g., wires) in a mold, before or after molding, treating at least one of the electrodes with one or more chemicals to change the electrical properties of the treated electrode upon contact with a fluid sample, and molding a body of insulative material around the electrodes with one end having therein means for receiving a fluid sample. The body may be molded in multiple pieces, e.g., two pieces, with a body and end cap for attaching to one another after the molding is completed, or in a single piece.

A sensor may be made by positioning electrodes on one or more substrates, the substrates including a first substrate, optionally contacting at least a portion of at least one electrode with sensing material(s), and configuring the sensor by positioning a spacer between the two substrates to maintain the substrates in a fixed, layered orientation relative to each other.

Application of the Sensors

A common use for a sensor of the present invention, such as sensor strip 10, 110, 210, 210' is for the determination of analyte concentration in a biological fluid, such as glucose concentration in blood, interstitial fluid, and the like, in a patient or other user. Additional analytes that may be determined include but are not limited to, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Sensors may be available at pharmacies, hospitals, clinics, from doctors, and other sources of medical devices. Multiple sensors may be packaged together and sold as a single unit; e.g., a package of about twenty five, about fifty, or about hundred sensors, or any other suitable number. A kit may include one or more sensors, and additional components such as control solutions and/or lancing device and/or meter, etc.

Sensors may be used for an electrochemical assay, or, for a photometric test. Sensors are generally configured for use with an electrical meter, which may be connectable to various electronics. A meter may be available at generally the same locations as the sensors, and sometimes may be packaged together with the sensors, e.g., as a kit.

Examples of suitable electronics connectable to the meter include a data processing terminal, such as a personal computer (PC), a portable computer such as a laptop or a handheld device (e.g., personal digital assistants (PDAs)), and the like. The electronics are configured for data communication with the receiver via a wired or a wireless connection. Additionally, the electronics may further be connected to a data network (not shown) for storing, retrieving and updating data corresponding to the detected glucose level of the user.

The various devices connected to the meter may wirelessly communicate with a server device, e.g., using a common standard such as 802.11 or Bluetooth RF protocol, or an IrDA infrared protocol. The server device could be another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touchscreen. With such an arrangement, the user can control the meter indirectly by interacting with the user interface(s) of the server device, which in turn interacts with the meter across a wireless link.

The server device may also communicate with another device, such as for sending data from the meter and/or the service device to a data storage or computer. For example, the service device could send and/or receive instructions (e.g., an insulin pump protocol) from a health care provider computer. Examples of such communications include a PDA synching data with a personal computer (PC), a mobile phone communicating over a cellular network with a computer at the other end, or a household appliance communicating with a computer system at a physician's office.

A lancing device or other mechanism to obtain a sample of biological fluid, e.g., blood, from the patient or user may also be available at generally the same locations as the sensors and the meter, and sometimes may be packaged together with the sensor and/or meter, e.g., as a kit.

The sensors are particularly suited for inclusion in an integrated device, i.e., a device which has the sensor and a second element, such as a meter or a lancing device, in the device. The integrated device may be based on providing an electrochemical assay or a photometric assay. In some embodiments, sensors may be integrated with both a meter and a lancing device. Having multiple elements together in one device reduces the number of devices needed to obtain an analyte level and facilitates the sampling process. For example, embodiments may include a housing that includes one or more of the sensor strips, a skin piercing element and a processor for determining the concentration of an analyte in a sample applied to the strip. A plurality of sensors may be retained in a cassette in the housing interior and, upon actuation by a user, a single sensor may be dispensed from the cassette so that at least a portion extends out of the housing for use.

Operation of the Sensor Strip

In use, a sample of biological fluid is provided into the sample chamber of the sensor, where the level of analyte is determined. The analysis may be based on providing an electrochemical assay or a photometric assay. In many embodiments, it is the level of glucose in blood that is determined. Also in many embodiments, the source of the biological fluid is a drop of blood drawn from a patient, e.g., after piercing the patient's skin with a lancing device, which could be present in an integrated device, together with the sensor strip.

After receipt of the sample in the sensor, the analyte in the sample is, e.g., electrooxidized or electroreduced, at the working electrode and the level of current obtained at the counter electrode is correlated as analyte concentration. The sensor may be operated with or without applying a potential to the electrodes. In one embodiment, the electrochemical reaction occurs spontaneously and a potential need not be applied between the working electrode and the counter electrode. In another embodiment, a potential is applied between the working electrode and the counter electrode.

The invention has been described with reference to various specific and preferred embodiments and techniques. However, it will be apparent to one of ordinary skill in the art that many variations and modifications may be made while remaining within the spirit and scope of the invention. It is understood that elements or features present on one embodiment described above could be used on other embodiments.

All patents and other references in this specification are indicative of the level of ordinary skill in the art to which this invention pertains. All patents and other references are herein incorporated by reference to the same extent as if each individual patent or reference was specifically and individually incorporated by reference.

What is claimed is:

1. A method of manufacturing a test strip, comprising:
   assembling said test strip having a test area including a test chemistry, said test area configured to collect a body fluid sample via capillary action and analyze said body fluid sample, said test area comprising an inlet having a width, said test area bound by a spacer layer on at least two sides; and
   forming a first skin contacting tab and a second skin contacting tab after said assembling,
   wherein the first and second skin contacting tabs are projections extending from a first edge of the test strip, wherein the first and second skin contacting tabs are proximate the inlet and have a width that is less than the inlet width.

2. The method of claim 1, wherein said assembling includes:
   disposing said test chemistry onto either a first panel or a second panel; and laminating said first panel to said second panel.

3. The method of claim 1, wherein said forming includes punching through the test strip.

4. The method of claim 1, wherein said forming includes punching through said test area.

5. The method of claim 1, wherein the width of the first and second skin contacting tabs is no more than about 80% of the inlet width.

6. The method of claim 1, wherein the first edge is a side edge of the test strip.

7. The method of claim 1, wherein the first edge is an end edge of the test strip.

8. The method of claim 1, wherein the test area includes only two inlets: a first inlet and a second inlet.

9. The method of claim 8, wherein the first and second skin contacting tabs are proximate the first inlet.

10. The method of claim 9, wherein the test strip comprises a third skin contacting tab and a fourth skin contacting tab, the third and fourth skin contacting tabs extending from a second edge of the test strip and wherein the third and fourth skin contacting tabs are proximate the second inlet.

11. The method of claim 9, wherein the first and second skin contacting tabs are located at the first inlet and the test strip comprises a third skin contacting tab and a fourth skin contacting tab, the third and fourth skin contacting tabs extending from a second edge of the test strip and wherein the third and fourth skin contacting tabs are located at the second inlet.

12. The method of claim 8, wherein the first and second skin contacting tabs are proximate the second inlet.

13. The method of claim 1, wherein said forming includes punching through the spacer layer.

14. A method of manufacturing a plurality of test strips, comprising:
   providing a first panel and a second panel wherein each of said first panel and said second panel includes a continuous sheet of material;
   disposing a test chemistry onto either said first panel or said second panel;
   assembling said first panel with said second panel and a spacer layer;
   forming a plurality of test strips after said assembling; and
   forming a first skin contacting tab and a second skin contacting tab for each of said plurality of test strips,
   wherein each of said plurality of test strips include a test area comprising said test chemistry and an inlet having a width, said test area bound by the spacer layer on at least two sides,
   wherein the first and second skin contacting tabs are projections extending from a first edge of each of said plurality of test strips and wherein the first and second skin contacting tabs are proximate the inlet and have a width that is less than the inlet width.

15. The method of claim 14, wherein said forming includes punching through said test area.

16. The method of claim 14, wherein the first edge is a side edge of the test strip.

17. The method of claim 14, wherein the first edge is an end edge of the test strip.

18. The method of claim 14, wherein the test area includes only two inlets: a first inlet and a second inlet.

19. The method of claim 18, wherein the first and second skin contacting tabs are proximate the first inlet.

20. The method of claim 19, wherein the test strip comprises a third skin contacting tab and a fourth skin contacting tab, the third and fourth skin contacting tabs extending from a second edge of the test strip and wherein the third and fourth skin contacting tabs are proximate the second inlet.

21. The method of claim 19, wherein the first and second skin contacting tabs are located at the first inlet and the test strip comprises a third skin contacting tab and a fourth skin contacting tab, the third and fourth skin contacting tabs extending from a second edge of the test strip and wherein the third and fourth skin contacting tabs are located at the second inlet.

22. The method of claim 18, wherein the first and second skin contacting tabs are proximate the second inlet.

23. The method of claim 14, wherein said forming includes punching through the spacer layer.

24. A method of manufacturing a test strip, comprising:
   assembling said test strip having a test area including a test chemistry, said test area configured to collect a body fluid sample via capillary action and analyze said body fluid sample, said test area comprising only two inlets: a first inlet and a second inlet, said test area bound by a spacer layer on at least two sides; and
   forming a first skin contacting tab and a second skin contacting tab after said assembling,
   wherein the first and second skin contacting tabs are projections extending from a first edge or a second edge of the test strip and wherein the first and second skin contacting tabs are proximate the first or the second inlet.

25. The method of claim 24, wherein the first and second skin contacting tabs are projections extending from a first edge of the test strip and are proximate the first inlet, wherein the test strip comprises a third skin contacting tab and a fourth skin contacting tab, the third and fourth skin contacting tabs extending from a second edge of the test strip and wherein the third and fourth skin contacting tabs are proximate the second inlet.

26. The method of claim 24, wherein the first and the second inlets comprise a width, wherein width of the first and second skin contacting tabs is less than the width of the first and the second inlets.

27. The method of claim 24, wherein said forming includes punching through the spacer layer.

\* \* \* \* \*